US012697107B2

(12) United States Patent
Pruckner et al.

(10) Patent No.: US 12,697,107 B2
(45) Date of Patent: *Aug. 4, 2026

(54) COUPLING ELEMENT FOR ATTACHING A MEDICAL OR DENTAL INSTRUMENT TO A CONTROL OR SUPPLY UNIT

(71) Applicant: W&H Dentalwerk Burmoos GmbH, Bürmoos (AT)

(72) Inventors: Christian Pruckner, Vienna (AT); Bernhard Silberer, Michaelbeuern (AT); Johann Eibl, Mattighofen (AT)

(73) Assignee: W&H Dentalwerk Bürmoos GmbH, Bürmoos (AT)

(*) Notice: Subject to any disclaimer, the term of this patent is extended or adjusted under 35 U.S.C. 154(b) by 336 days.

This patent is subject to a terminal disclaimer.

(21) Appl. No.: 18/535,838

(22) Filed: Dec. 11, 2023

(65) Prior Publication Data

US 2024/0099705 A1 Mar. 28, 2024

Related U.S. Application Data

(63) Continuation of application No. 17/121,663, filed on Dec. 14, 2020, now Pat. No. 11,871,915, which is a
(Continued)

(30) Foreign Application Priority Data

Mar. 27, 2015 (EP) ..................................... 15161217

(51) Int. Cl.
*A61B 17/00* (2006.01)
*A61C 1/00* (2006.01)

(52) U.S. Cl.
CPC ............ *A61B 17/00* (2013.01); *A61C 1/0015* (2013.01); *A61B 2017/00022* (2013.01); *A61B 2017/00411* (2013.01); *A61B 2017/00477* (2013.01)

(58) Field of Classification Search
CPC .......... A61B 17/00; A61B 2017/00022; A61B 2017/00411; A61B 2017/00477;
(Continued)

(56) References Cited

U.S. PATENT DOCUMENTS 5,074,785 A 12/1991 Malata, Jr.
2003/0165794 A1 9/2003 Matoba
(Continued)

FOREIGN PATENT DOCUMENTS

EP 2184028 5/2010
EP 2514386 10/2012
(Continued)

OTHER PUBLICATIONS

International Search Report for PCT-EP2016-056301, mailed Jun. 2, 2016.

*Primary Examiner* — Scott M. Getzow
(74) *Attorney, Agent, or Firm* — Klarquist Sparkman, LLP

(57) ABSTRACT

A medical or dental instrument part having a coupling device, a medical or dental instrument part controller, at least one sensor which is configured to generate a sensor signal and three electrical lines, wherein a first shared electric line and a second shared electric line of the three electrical lines connect the medical or dental instrument part controller and an electromagnetic radiation emitting device to a shared electrical power source to supply electrical power from the shared electrical power source, and wherein a third electric line of the three electric lines connects the medical or dental instrument part controller and the sensor to a control, regulating or supply unit, so that the sensor signal can be transmitted to the control, regulating or supply unit.

20 Claims, 4 Drawing Sheets

Related U.S. Application Data continuation-in-part of application No. 15/712,081, filed on Sep. 21, 2017, now Pat. No. 10,932,883, which is a continuation of application No. PCT/EP2016/056301, filed on Mar. 23, 2016.

(58) Field of Classification Search
CPC .......... A61B 2017/00084; A61B 90/98; A61B 2017/00482; A61C 1/0015
See application file for complete search history.

(56) References Cited

U.S. PATENT DOCUMENTS

| | | |
|---|---|---|
| 2004/0209223 A1 | 10/2004 | Beier et al. |
| 2007/0031778 A1 | 2/2007 | Helfenbein et al. |
| 2007/0054232 A1 | 3/2007 | Rauchenzauner |
| 2008/0116326 A1 | 5/2008 | Schiebler |
| 2008/0145817 A1* | 6/2008 | Brennan .................. A61C 1/08 |
| | | 433/98 |

| | | |
|---|---|---|
| 2008/0176181 A1 | 7/2008 | Putz et al. |
| 2010/0109644 A1 | 5/2010 | Pruckner et al. |
| 2010/0248177 A1 | 9/2010 | Mangelberger et al. |
| 2015/0037751 A1 | 2/2015 | Motoyama |
| 2016/0058525 A1 | 3/2016 | Nichols et al. |

FOREIGN PATENT DOCUMENTS

| | | |
|---|---|---|
| EP | 2727552 | 5/2017 |
| EP | 3636203 | 4/2020 |
| JP | 2002035009 | 2/2002 |
| JP | 2002336281 | 11/2002 |
| JP | 2006334416 A | 12/2006 |
| JP | 2011130860 A | 7/2011 |
| JP | 2014-528782 A | 10/2014 |
| JP | 2015536716 A | 12/2015 |
| JP | 2018512225 A | 5/2018 |
| JP | 2018518223 A | 7/2018 |
| JP | 2019-517864 A | 9/2019 |

* cited by examiner

COUPLING ELEMENT FOR ATTACHING A MEDICAL OR DENTAL INSTRUMENT TO A CONTROL OR SUPPLY UNIT

CROSS REFERENCE TO RELATED APPLICATION

This application is a Continuation of U.S. patent application Ser. No. 17/121,663, filed Dec. 14, 2020, which is a Continuation-in-Part of U.S. patent application Ser. No. 15/712,081, filed Sep. 21, 2017, which is a U.S. bypass continuation of International Application No. PCT/EP2016/056301, filed Mar. 23, 2016, which in turn claims priority from pending European Patent Application No. 15161217.3, filed Mar. 27, 2015, which are incorporated herein by reference.

BACKGROUND

Field

The present application relates to a medical or dental instrument part with a memory device that can be operated with electrical power for storing identification data and/or operating data and/or care data of or for the instrument part.

Description of Prior Art

A medical or dental instrument part with a memory device that can be operated with electrical power is known from the patent application US 2003/0165794 A1 (also published as U.S. Pat. No. 6,899,538), for example. This memory device is part of an identification signal output device for active output of identification signals to identify the instrument part so that a circuit of a control, regulating or supply unit automatically recognizes the instrument part and supplies it or drives it accordingly. The power supply and communication between the memory device and the drive circuit are hardwired and take place via electrical lines, which electrically connect the memory device and the control, regulating or supply unit.

SUMMARY

An object of the present application is to improve the design of a medical or dental instrument part with regard to the hardwired power supply and communication link/data transmission between the memory device and the control, regulatory or supply unit. In particular, the design of the instrument part should be simple and components forming the power supply and communication link between the memory device and the control, regulating or supply unit should take up little space and ensure a reliable power supply and data transmission.

These objects are achieved by a medical or dental instrument part, by a medical or dental treatment device and by a method for operating a medical or dental instrument part or a medical or dental treatment device having the features described below. The medical or dental instrument part comprises: a coupling device for connection of the instrument part to a control, regulating or supply unit, a memory device that can be operated with electrical power for storing identification data and/or operating data and/or care data of the instrument part and at least one electrical line, which is provided for supplying electrical power to a lighting device that is provided on the instrument part or is or can be connected to the instrument part for operation of the lighting device and for supplying electrical power to the memory device for operation of the memory device.

The design of the instrument part is greatly simplified due to the fact that at least one electrical line is provided for supplying electrical power to the lighting device for operation of the lighting device and for supplying electrical power to the memory device for operating the memory device. Thus, for example, the number of electrical lines in the instrument part is reduced. In particular the design of the coupling device for connecting the instrument part to a control, regulating or supply unit is greatly simplified because the number of electrical contacts on the interface of the coupling device is reduced.

The at least one electrical line which is provided for supplying electrical power to the lighting device that is provided on the instrument part or can be connected to the instrument part for operating the lighting device and for supplying electrical power to the memory device for operating the memory device is preferably designed as a joint or shared electrical line, in particular as a joint electrical line for the lighting device and the memory device. The lighting device and the memory device are thus in particular electrically connected to the (joint) electrical line. A branching point, from which a first electrical branch line extends to the memory device and a second electrical branch line extends to the lighting device, is provided in particular.

The at least one (joint) electrical line is preferably designed as a wire line and/or as an electrical line printed on a circuit board.

The term "medical or dental instrument part" is understood below as follows: a medical or dental element that can be held in a hand, a hand grip element, a straight handpiece, an angled or bent handpiece or a contra-angled handpiece, an adapter, a coupling element, a drive element in particular an air motor or an electric motor or a supply tube or a part of one of the elements listed above.

The instrument part preferably comprises a medical or dental handpiece or at least one part thereof including: a drive element that can be set in rotation for driving a tool that is releasably connectable to the handpiece, a coupling device for connecting the handpiece to a control, regulating or supply unit, a memory device that can be operated with electrical power for storing identification data and/or operating data or care data of the handpiece, a lighting device that can be operated with electrical power for emitting radiation to a treatment site, and at least one (joint) electrical line, which is provided for supplying electrical power to the lighting device for operating the lighting device and for supplying electrical power to the memory device for operating the memory device.

The coupling device for connecting the instrument part to a control, regulating or supply unit is in particular designed as a releasable coupling device, so that the instrument part can be separated from the control, regulating or supply unit. The coupling device is designed, for example, as a plug coupling or as a pivoting coupling, so that the instrument part can be rotated in relation to the control, regulating or supply unit, when the instrument part is connected to the control, regulating or supply unit via the coupling device.

The coupling device comprises in particular an end face, on which at least one electrical contact that is connected to the at least one joint electrical line, is provided. When two joint electrical lines are provided, there are preferably two electrical contacts disposed on the end face of the coupling device, wherein one of the two electrical contact is connected to one of the two joint electrical lines, respectively. When at least one separate optical or electrical line is provided for transmitting identification data and/or operating data and/or care data, then an optical or electrical contact that is connected to this at least one electrical line for data transmission is preferably provided accordingly.

The at least one electrical contact or the electrical contacts is/are preferably releasably connected to the control, regulating or supply unit. The at least one electrical contact is, for example, preferably designed as a pin-shaped electrical contact, as a spring contact, as a sliding contact or as a ring-shaped electrical contact surrounding a component of the coupling device.

The memory device comprises either a read-only memory (ROM) or preferably a readable and writable memory. The memory device is designed in particular as a digital memory device for storage and/or readout and/or processing of digital data.

In particular identification data and/or operating data and/or care data assigned to that instrument part in which the memory device is disposed, is are preferably stored or can be stored in the memory device of the instrument part. Alternatively, it is also conceivable that identification data and/or operating data and/or care data from another instrument part other than the instrument part, in which the memory device is disposed is or can be stored additionally or exclusively in the memory device.

The memory device preferably comprises a memory element and a microcontroller or microcomputer, which is/are optionally designed as one component or as two separate components electrically connected to one another. If the memory element and the microcontroller are embodied separately from one another, then it is possible to position them at different locations in/on the instrument part so that the arrangement of the two components in an instrument part with a small internal volume is facilitated.

The memory device with the microcontroller is preferably designed for active output of a digital signal or digital data. The memory device with the microcontroller also comprises in particular software enabling it to receive, send, process, store data and/or to carry out independent control steps.

The supply of electrical power to the lighting device and the memory device and preferably the (digital) data transmission over the at least one (joint) electrical line is/are implementable, for example, by modulation and/or digital multiplexing and/or by time offset transmission or sending of digital data and/or electrical power, in particular being implementable with the help of the microcontroller of the memory device.

The lighting device that is provided on the instrument part or can be connected to the instrument part preferably comprises one or more light sources, for example, optical semiconductor elements, in particular light-emitting diodes (LEDs). The lighting device preferably comprises a plurality of light sources, wherein at least one first light source (LED) emits a first wavelength or a first wavelength range, and at least one second light source (LED) emits a second wavelength or a second wavelength range, which differs from the first wavelength or the first wavelength range. The first light source and the second light source are preferably disposed in different electrical current directions. A switching device for optional operation of the first light source or the second light source and/or for optional emission of electromagnetic radiation by the first light source or by the second light source is especially preferred provided on the instrument part. In particular the switching device is connected to the microcontroller or designed as part of the microcontroller or is provided on an element that is or can be connected to the instrument part, for example, the control, regulating or supply unit. The switching device especially preferred controls the optional operation of the first light source or the second light source over the at least one (joint) electrical line. The switching device is especially preferred designed as an electrical switching device, for example, as an H bridge.

If the instrument part is designed as a medical or dental handpiece, as is described above, then the lighting device is preferably disposed on or adjacent to a head part of the handpiece, in which the tool holder for the releasably connectable tool is mounted. In particular the lighting device comprises a plurality of optical semiconductor elements positioned in a ring around a tool receptacle opening of the head part.

Alternatively, the instrument part with the memory device, in particular with the microcontroller, does not comprise a lighting device but instead comprises only at least one (joint) electrical line, which is provided not only for supplying electrical power to the memory device, but which is also provided for supplying electrical power to a lighting device. The lighting device is disposed in another element, which is or can be connected to the instrument part with the memory device, so that the lighting device can be supplied with electrical power over the at least one (joint) electrical line.

According to an embodiment, no more than two (joint) electrical lines are provided for supplying electrical power to the lighting device for operating the lighting device and for supplying electrical power to the memory device for operating the memory device and for transmitting identification data and/or operating data and/or care data between the memory device and the control, regulating or supply unit connectable to the instrument part. Both the supply of electrical power to the lighting device and to the memory device and the data transmission thus take place exclusively by way of these two (joint) electrical lines. This embodiment is thus the simplest or optimal embodiment with respect to the design of the medical or dental instrument part, the number of electrical contacts on the coupling device and the space required.

According to an alternative embodiment, at least one separate line is provided for transmitting identification data and/or operating data and/or care data between the memory device and the control, regulating or supply unit that can be connected to the instrument part. This separate line (hereinafter also referred to as a data line) is thus, preferably exclusively provided for data transmission between the memory device and the control, regulating or supply unit, but it is not provided for the supply of electrical power to the lighting device and the memory device. The separate data line may be designed, for example, as an electrical line for transmitting electrical (data) signals or as an optical line, for example, as a glass fiber for transmitting optical (data) signals. The data line especially preferred forms a direct connection between the microcontroller of the memory device of the instrument part and the control, regulating or supply unit, in particular another microcontroller disposed in the control, regulating or supply unit.

This alternative embodiment thus preferably comprises three lines for supplying electrical power to the lighting device and to the memory device and for transmitting the identification data and/or operating data and/or care data between the memory device and the control, regulating or supply unit. These three lines in particular include at least two electrical lines for supplying electrical power to the lighting device and to the memory device and optionally a third electrical or optical line for data transmission. Accordingly, three electrical contacts or two electrical contacts and one optical contact are provided on the coupling device of the instrument part, wherein each contact is connected a corresponding one of the three lines.

The lighting device and the memory device are preferably disposed in parallel electrically with the microcontroller, in particular including a voltage device assigned to the memory device.

Preferably, an electrical switching element is provided which is assigned to the memory device in particular and which is designed to trigger changes in an electrical current parameter, in particular the electrical voltage for transmission of identification data and/or operating data and/or care data between the memory device and the control, regulating or supply unit that can be connected to the instrument part. The electrical switching element is preferably provided for supporting the readout or for reading out data from the memory device, in particular for transmitting data from the memory device to the control, regulating or supply unit. The electrical switching element preferably opens and closes a circuit between the memory device and the control, regulating or supply unit so that an electrical current parameter, in particular the electrical voltage is variable, for example, an electrical current parameter of the electrical power for supplying power to the lighting device and the memory device. The electrical switching element is preferably connected electrically to the at least one (joint) electrical line. The at least one (joint) electrical line is preferably part of this circuit. As will be described in detail below, the control, regulating or supply unit is preferably designed to receive the change in the electrical current parameter, wherein the change in the electrical parameter and/or the reaction of the control, regulating or supply unit define(s) the transmitted identification data and/or operating data and/or care data, in particular digitally.

The electrical switching element is preferably designed to short circuit the shunt resistor described in the following paragraph for readout of data from the memory device.

A shunt resistor, in particular one assigned to the memory device, is preferably provided and is designed to process changes in the electrical amperage for transmission of identification data and/or operating data and/or care data between the memory device and the control, regulating or supply unit that can be connected to the instrument part. The shunt resistor is preferably provided for or supports the storage of data in the memory device, in particular for transmitting data from the control, regulating or supply unit to the memory device. The shunt resistor preferably converts values of the electrical amperage of the control, regulating or supply unit which (digitally) define identification data and/or operating data and/or care data, into voltage values which can be processed by the memory device and which (digitally) define identification data and/or operating data and/or care data. The shunt resistor is preferably electrically connected to the at least one (joint) electrical line.

Alternatively or additionally, the shunt resistor is preferably designed for monitoring the current for the lighting device, in particular for the at least one optical semiconductor element. In particular the shunt resistor prevents the lighting device from being supplied with an electrical amperage that is too high.

Preferably, a device for voltage processing is provided which is designed to supply a constant electrical voltage to the memory device, in particular the microcontroller and which is assigned to the memory device, in particular the microcontroller. In particular the voltage processing device forms a constant voltage source for the memory device, in particular the microcontroller. The voltage processing device is preferably electrically connected to a power source, in particular to an electrical constant current source in the control, regulating or supply unit, in particular being connected via at least one (joint) electrical line. The energy source, in particular the constant current source in the control, regulating or supply unit, preferably supplies electrical power to the voltage processing device. The voltage processing device is preferably designed so that the memory device, in particular the microcontroller is supplied with a lower electrical voltage than the lighting device. The voltage processing device is preferably connected in series to the memory device.

Preferably, a device for monitoring the voltage is provided which is assigned to the lighting device and which is designed to monitor the electrical voltage supplied to the lighting device. The voltage monitoring comprises in particular a voltage divider, which monitors the input voltage on the instrument part. The voltage divider has, for example, two electrical resistors, which are connected to the microcontroller of the memory device.

According to an embodiment, the instrument part comprises at least one sensor, which is designed to detect the operating state of the instrument part and to generate a sensor signal, preferably an electrical signal, wherein the at least one sensor is electrically connected to the at least one (joint) electrical line so that the sensor signal of the sensor and/or the electrical power for operating the sensor is are transmissible over the at least (joint) electrical line.

The sensor comprises, for example, a temperature sensor for measuring the temperature of the instrument part or of a portion thereof or of at least a component disposed in the instrument part, in particular a component that can be set in motion by a drive element, for example, a bearing. The temperature sensor comprises in particular an electrically operable temperature sensor, for example, a temperature sensor having a material whose electrical resistance changes with the temperature (e.g., NCT temperature sensor) or an infrared temperature sensor.

Alternatively, the sensor comprises a speed sensor, for example, for measuring the rotational speed of a drive element of the instrument part or a tool that can be connected thereto. The speed sensor is designed, for example, as an inductive, capacitive or optical speed sensor.

The sensor may of course also be designed to measure other parameters and may comprise, for example, a sensor for measuring power, force or pressure, torque, light intensity or wavelength, etc.

The sensor signal is preferably sent over the at least one (joint) electrical line, or alternatively, over the separate data line described above to the control, regulating or supply unit, in particular to a microcontroller disposed therein. The at least one sensor is thus connected in particular via the at least one (joint) electrical line or via the separate data line to the control, regulating or supply unit in such a way that the control, regulating or supply unit receives a sensor signal and processes it. In particular the control, regulating or supply unit is designed to control or regulate the instrument part based on a sensor signal received from the at least one sensor or to supply said instrument part, for example, with an operating medium.

According to an embodiment, a medical or dental treatment device is provided, comprising: a medical or dental instrument part as described above or below, an electrical power source, in particular a constant current source, which is designed to supply the lighting device and the memory device of the instrument part with electrical power, and a control, regulating or supply unit, which is designed for exchanging identification data and/or operating data and/or care data of the instrument part with the memory device of the instrument part. The instrument part and the control, regulating or supply unit are preferably releasably connected to one another by the coupling device.

Another microcontroller, which is connected to the microcontroller of the instrument part is preferably provided in the control, regulating or supply unit, wherein the at least one (joint) electrical line forms a part of this connection, Preferably the power source is also disposed in the control, regulating or supply unit and in particular is connected electrically to the lighting device and the memory device by the at least one (joint) electrical line.

As already described above, the power source, in particular the constant current source, supplies the lighting device with a constant amperage. The memory device, in particular the microcontroller, which requires a constant electrical voltage is supplied with electrical power from the power source which is designed preferably as a constant current source via a device for voltage processing assigned to the memory device. The device for voltage processing is designed to supply a constant electrical voltage to the memory device.

Preferably the control, regulating or supply unit, in particular its microcontroller is designed to detect or recognize changes in the electrical load or the electrical voltage, which are in particular triggered by the switching element, for readout of the identification data and/or operating data and/or care data stored in the memory device.

As already described above, the electrical switching element preferably opens and closes a circuit between the memory device and the control, regulating or supply unit and in particular short-circuits the shunt resistor assigned to the memory device, so that an electrical current parameter, in particular the electrical voltage, which defines the identification data and/or operating data and/or care data (digitally) can be varied. The control, regulating or supply unit, in particular its microcontroller is/are designed to detect or recognize the changes or fluctuations triggered by the switching element. The change in the current parameter and/or the equalization of these fluctuations in the electrical current parameter are detected by the microcontroller of the control, regulating or supply unit and the identification data and/or operating data and/or care data transmitted from the memory device is thereby derived.

The electrical power source, in particular the constant current source and/or the control, regulating or supply unit is/are preferably designed to vary the electrical amperage, which can be supplied to the shunt resistor, which in particular is assigned to the memory device, and to the memory device for transmission of data to the memory device. The microcontroller of the control, regulating or supply unit is designed in particular to trigger or control the change in the electrical amperage. The change in amperage defines, digitally in particular, the identification data and/or operating data and/or care data. As described above, a shunt resistor preferably converts the values of the electrical amperage of the control, regulating or supply unit, which define identification data and/or operating data and/or care data, into electrical voltage values, which can be received and processed by the microcontroller of the instrument part so that the microcontroller can store data on the memory element of the memory device.

The control, regulating or supply unit is preferably designed to operate the instrument part based on identification data and/or operating data and/or care data stored in the memory device and read out of the memory device and/or on the basis of the sensor signal received from the at least one sensor. For example, the control, regulating or supply unit is designed to supply the drive power coordinated with this instrument part on the basis of this data and/or to supply at least a certain medium and/or a certain amount of one or more media.

The control, regulating or supply unit is preferably designed to transmit data to the instrument part, for example, with respect to the duration of operation of the instrument part, the type of use thereof and/or the type and/or duration of the cleaning and/or care thereof.

According to an embodiment a method for operating a medical or dental instrument part or a medical or dental treatment device is provided, in which at least one (joint) electrical line supplies electrical power to a lighting device that is provided on the instrument part or is or can be connected to the instrument part for operation of the lighting device and also supplies electrical power to a memory device for operation of said memory device.

Preferably no more than two electrical lines supply electrical power to the lighting device for operation of the lighting device and to the memory device for operation of the memory device and transmit the identification data and/or operating data and/or care data between the memory device and the control, regulating or supply unit that can be connected to the instrument part. Alternatively, at least one separate line. (data line) transmits the identification data and/or operating data and/or care data, in particular directly, between the memory device and the control, regulating or supply unit that can be connected to the instrument part. The data line is optionally designed as an electrical line, which transmits the data in the form of electrical signals or as an optical line, which transmits the data in the form of optical signals.

The at least one (joint) electrical line preferably additionally transmits a sensor signal of the sensor in the instrument part and/or electrical power for operating the sensor as described above.

The control, regulating or supply unit, in particular its microcontroller, preferably detect(s) car recognizes) changes in an electrical current parameter, in particular the electrical voltage caused by the switching element for readout of the identification data and/or operating data and/or care data stored in the memory device. The microcontroller of the control, regulating or supply unit detects the change in the electrical current parameter and/or the equalization of these fluctuations and therefrom recognizes the identification data and/or operating data and/or care data transmitted by the memory device as described above.

For transmitting data to the memory device the electrical power source, in particular the constant current source and/or the control, regulating or supply unit preferably vary/varies the electrical amperage, which is supplied to the shunt resistor and to the memory device. The shunt resistor preferably converts the values of the electrical amperage of the control, regulating or supply unit, which define the identification data and/or operating data and/or care data, into electrical voltage values, which define identification data and/or operating data and/or care data (digitally). These electrical voltage values are received or processed and stored in the memory element by the microcontroller of the instrument part, as described above.

The control, regulating or supply unit preferably operates the instrument part on the basis of identification data and/or operating data and/or care data stored in the memory device and read out of the memory device and/or on the basis of the sensor signal received from the at least one senor, as described above.

According to an embodiment there is provided: A medical or dental instrument part, comprising: a coupling device which couples the medical or dental instrument part to a supply tube for connection of the medical or dental instrument part to a control, regulating or supply unit; a medical or dental instrument part controller operable with electrical power; and three electrical lines comprising a first shared electric line, a second shared electric line and a third electric line. The first shared electric line and the second shared electric line connect to the medical or dental instrument part controller and to an electromagnetic radiation emitting device that is provided on the medical or dental instrument part or can be connected to the medical or dental instrument part and supply electrical power from a shared electrical power source to the electromagnetic radiation emitting device for operating the electromagnetic radiation emitting device and to the medical or dental instrument part controller for operating the medical or dental instrument part controller. The third electric line of the three electric lines connects the medical or dental instrument part controller to the control, regulating or supply unit. The medical or dental instrument part further comprises at least one sensor which is configured to generate a sensor signal, wherein the at least one sensor is connected to the third electric line so that the sensor signal of the sensor can be transmitted over the third electric line to the control, regulating or supply unit.

The medical or dental instrument part controller preferably comprises a microcontroller or microcomputer. The medical or dental instrument part controller preferably comprises a memory element for storing identification data and/or operating and/or care data of the medical or dental instrument part.

The electromagnetic radiation emitting device emits electromagnetic radiation from the medical or dental instrument part or from a component coupled to the medical or dental instrument part. The electromagnetic radiation emitting device emits electromagnetic radiation towards a workpiece of the medical or dental instrument part. The electromagnetic radiation emitted by the electromagnetic radiation emitting device comprises at least one of: visible radiation or visible light, i.e. radiation having at least one wavelength in the range between 380 nm-780 nm; white light; non-visible radiation, i.e. radiation having wavelengths outside the range of 380 nm-780 nm; laser light; IR-radiation; UV-radiation; radiation for diagnosis; radiation for treatment of tissue.

The shared electrical power source supplies electric power to the medical or dental instrument part controller and to the electromagnetic radiation emitting device. The shared electrical power source preferably supplies electric power to the at least one sensor of the medical or dental instrument part, in particular if the at least one sensor is an active sensor which needs electric power to operate. The shared electrical power source may supply electric power to additional components of the medical or dental instrument part or coupled to the medical or dental instrument part, e.g., a display or a heating element.

The shared electrical power source may comprise a constant current source supplying electric power having a constant amperage or a constant voltage source supplying electric power having a constant voltage.

The third electric line of the three electric lines is provided for the transmission of data between the control, regulating or supply unit and components of the medical or dental instrument part, in particular the at least one sensor and/or the medical or dental instrument part controller. Preferably, the first shared electric line and the second shared electric line only supply electric energy to the medical or dental instrument part, while the third electric line transmits sensor signals and/or data only, so that advantageously the supply of electric power and the transmission of sensor signals and/or data is accomplished on different, separated electric lines, which preferably results at least in less interferences between the supplied electric energy and the transmitted sensor signals and/or data and thus in a more stable sensor signal and/or data transmission.

The transmission of data via the third electric line may comprise a unidirectional transmission, e.g., the transmission of the sensor signal from the at least one sensor to the control, regulating or supply unit, in particular when the at least one sensor is an analog sensor. The transmission of data may comprise a bidirectional transmission, e.g., the transmission of data between the memory element of the medical or dental instrument part controller and the control, regulating or supply unit and/or when the at least one sensor is a digital sensor.

The at least one sensor is connected to the third electric line for the transmission of the sensor signal or a signal derived from the sensor signal. The at least one sensor may be connected directly to the third electric line, i.e. without any intermediate component between the at least one sensor and the third electric line.

Alternatively, the at least one sensor is connected to the third electric line via the medical or dental instrument part controller. Preferably, the at least one sensor is connected electrically to the medical or dental instrument part controller, in particular through electric lines. Thus, the sensor signal of the at least one sensor is transmitted to the medical or dental instrument part controller. Preferably, the sensor signal as generated by the at least one sensor or a sensor signal processed by the medical or dental instrument part controller or a signal derived from the sensor signal is transmitted from the medical or dental instrument part controller and the third electric line to the control, regulating or supply unit.

The third electric line may comprise a shared electric line which connects to a plurality of components of one medical or dental instrument part or of a plurality of medical or dental instrument parts, e.g., to the at least one sensor and to the medical or dental instrument part controller.

The medical or dental instrument part controller preferably supplies electric power to the at least one sensor, in particular if the at least one sensor is an active sensor which needs electric power to operate. The medical or dental instrument part controller is especially preferred configured to process the electric power received via the first shared electric line and the second shared electric line from the shared electric power source and to supply the processed electric power to the at least one sensor, so that the at least one sensor is supplied with the electric power that it requires. The medical or dental instrument part controller supplies electric power to the at least one sensor via electric lines, wherein at least one of these electric lines for power supply may in particular be used for the transmission of the sensor signal to the medical or dental instrument part controller.

Alternatively, the at least one sensor is connected directly (i.e. without the medical or dental instrument part controller being inserted between the at least one sensor and the first and second shared electric lines via the first and second shared electric lines to the shared electrical power source to receive electrical power from the shared electrical power source. Preferably a device for processing the electrical power supplied from the shared electrical power source is assigned to the at least one sensor to supply only the at least one sensor with the electric power that it requires. For example, the device for processing the electrical power comprises a DC/DC converter.

Preferably, the medical or dental instrument part controller is configured to at least one of store or process the sensor signal generated by the at least one sensor.

Processing the sensor signal may preferably comprise converting the sensor signal generated by the at least one sensor. For example, if the sensor signal is an analog sensor signal the medical or dental instrument part controller is configured to convert the analog sensor signal into a digital sensor signal.

Processing the sensor signal may preferably comprise filtering the sensor signal generated by the at least one sensor. Processing the sensor signal may preferably comprise reducing the noise of the sensor signal generated by the at least one sensor. Processing the sensor signal may preferably comprise amplifying the sensor signal generated by the at least one sensor.

The medical or dental instrument part controller is preferably configured to store the processed sensor signal and/or to send the processed sensor signal, in particular the converted digital sensor signal, to the control, regulating or supply unit via the third electric line of the three electric lines.

The medical or dental instrument part controller preferably is configured to operate or regulate or control at least one component of the medical or dental instrument based on the sensor signal received from the at least one sensor. Especially preferred the medical or dental instrument part controller stores and/or processes the sensor signal as described above before operating or regulating or controlling at least one component of the medical or dental instrument based on the sensor signal.

For example, based on the sensor signal the medical or dental instrument part controller may start or stop or accelerate or break the drive or motion of a component of the medical or dental instrument part. Alternatively or in addition, based on the sensor signal the medical or dental instrument part controller may start or stop the emission of electromagnetic radiation of the electromagnetic radiation emitting device and/or vary one of the radiation intensity, the wavelength of the radiation to be emitted by the electromagnetic radiation emitting device. Alternatively or in addition, based on the sensor signal the medical or dental instrument part controller may start or stop the delivery of a medium, fluid, water, air, medicine or diagnostic agent. Alternatively or in addition, based on the sensor signal the medical or dental instrument part controller may start or stop the determination, measurement, recording of a value, in particular through a sensor, or the capturing of an image, in particular through a sensor or camera.

Preferably the memory element connects to the third electric line so that the identification data and/or operating and/or care data of the medical or dental instrument part can be transmitted over the third electric line between the control, regulating or supply unit and the memory element. The third electric line thus serves for the transmission of the sensor signal of the at least one sensor and of identification data and/or operating and/or care data, which advantageously reduces the number of electrical lines in the medical or dental instrument part.

The medical or dental instrument part preferably comprises a device for processing electrical power which is configured to process the electrical power supplied by the shared electrical power source via the first or second shared electric line to the medical or dental instrument part.

In particular the device for processing electrical power is configured to provide electrical power having constant voltage or direct current. Alternatively, the device for processing electrical power is configured to provide electrical power having constant amperage or alternating current.

The device for processing electrical power may provide processed electrical power, preferably electrical power having constant voltage or direct current, for a plurality of elements of the medical or dental instrument part supplied with electric power, for example for at least two or all of the following elements: the medical or dental instrument part controller; the at least one sensor; the electromagnetic radiation emitting device; other components.

Alternatively, the device for processing electrical power is assigned to a single element of the medical or dental instrument part supplied with electric power and may provide processed electrical power, preferably electrical power having constant voltage or direct current, for said single element to which it is assigned only. For example, the device for processing electrical power is assigned to and provides electrical power for one of the following elements of the medical or dental instrument part only: the medical or dental instrument part controller; at least one sensor; the electromagnetic radiation emitting device; another component.

The device for processing electrical power may comprise an AC/DC converter or rectifier. For example, the AC/DC converter is configured to convert electric power having a constant amperage and supplied by the shared electrical power source comprising a constant current source via the first and second shared electric lines to electric power having a variable voltage. Preferably the AC/DC converter or rectifier may be formed by electronic components or by an electronic or integrated circuit. Especially preferred the AC/DC converter or rectifier is configured or arranged such that it provides direct current for all electrical components of the medical or dental instrument part, in particular for the medical or dental instrument part controller, the at least one sensor and the electromagnetic radiation emitting device.

The device for processing electrical power may comprise an DC/AC converter or inverter. For example, the DC/AC converter is configured to convert electric power having a constant voltage and supplied by the shared electrical power source comprising a constant voltage source via the first and second shared electric lines to electric power having a constant amperage. Preferably the DC/AC converter or inverter may be formed by electronic components or by an electronic or integrated circuit.

An AC/DC converter is preferably assigned to the electromagnetic radiation emitting device only and provides power having a constant amperage to the electromagnetic radiation emitting device only. Especially preferred the AC/DC converter assigned to the electromagnetic radiation emitting device only forms part of a constant current source which is assigned to the electromagnetic radiation emitting device only.

The device for processing electrical power may comprise a DC/DC converter. The DC/DC converter may preferably be assigned to and/or provide electric power for a plurality of elements supplied with electric power of the medical or dental instrument part, for example for at least two or all of the following elements: the medical or dental instrument part controller; the at least one sensor; the electromagnetic radiation emitting device; other components. Alternatively or in addition there may be provided a DC/DC converter which is assigned to and/or processes electric power for a single element supplied with electric power of the medical or dental instrument part only, for example for only one of the following elements: the medical or dental instrument part controller; the at least one sensor; the electromagnetic radiation emitting device; another component. Preferably the DC/DC converter may be formed by electronic components or by an electronic or integrated circuit.

The device for processing electrical power may comprise a filter, for example to compensate for transmission interference of the electrical power supplied by the shared electrical power source via the first and second shared electric line. Again, the filter may either be assigned to single element supplied with electric power of the medical or dental instrument part only and filter the electric power for said single element to which it is assigned only or to a plurality or all electric elements of the medical or dental instrument part and filter the electric power for said plurality of or all elements as described above.

The medical or dental instrument part preferably comprises an electrical constant current source which is assigned to the electromagnetic radiation emitting device only and which is configured to supply only the electromagnetic radiation emitting device with electrical power having a constant amperage. The electrical constant current source connects via the first and second shared electric lines to the shared electrical power source to receive electrical power from the shared electrical power source to operate the electromagnetic radiation emitting device. Preferably the shared electrical power source is formed or comprises a constant voltage power source. Preferably the electrical constant current source receives electric power having constant voltage or direct current.

Preferably the electrical constant current source may be formed by electronic components or by an integrated circuit. Preferably the integrated circuit is configured to convert electric power having constant voltage or direct current to electric power having constant amperage or alternating current. Preferably the electrical constant current source may comprise a shunt resistor.

The medical or dental instrument part controller is preferably configured to control the electromagnetic radiation emission of the electromagnetic radiation emitting device. Especially preferred the medical or dental instrument part controller is configured to control the intensity of the electromagnetic radiation emitted by the electromagnetic radiation emitting device. Especially preferred the medical or dental instrument part controller is configured to dim the electromagnetic radiation emitting device, in particular to dim visible light emitted by the electromagnetic radiation emitting device. Especially preferred the medical or dental instrument part controller is configured to control the afterglow of the electromagnetic radiation emitting device, in particular the afterglow of visible light emitted by the electromagnetic radiation emitting device, so that electromagnetic radiation is emitted by the electromagnetic radiation emitting device when another operation of the medical or dental instrument part controller is stopped, e.g., the drive of a tool connected to the medical or dental instrument part controller and/or the delivery of a fluid.

To control the electromagnetic radiation emission of the electromagnetic radiation emitting device the medical or dental instrument part controller is preferably connected to the electrical constant current source which is assigned to the electromagnetic radiation emitting device. Especially preferred the medical or dental instrument part controller is communicatively connected to the electrical constant current source. Especially preferred the medical or dental instrument part controller is configured to communicate control signals to the electrical constant current source to control the emission of electromagnetic radiation by the electromagnetic radiation emitting device. Especially preferred the medical or dental instrument part controller and the electromagnetic radiation emitting device, in particular the electrical constant current source, are communicatively connected with one another through electric control lines. Especially preferred the electrical constant current source of the electromagnetic radiation emitting device is configured to receive control signals of the medical or dental instrument part controller and to operate the electromagnetic radiation emitting device according to the received control signals.

With reference to each embodiment described above and in the following, and unless explicitly described otherwise, the at least one sensor of the medical or dental instrument part may comprise at least one of the following sensors: a mechanical sensor; a capacitive sensor; an inductive sensor; an optical or optoelectronic sensor, in particular an image capturing sensor, a camera or a sensor detecting an electromagnetic radiation intensity or a wavelength; a magnetic sensor, in particular a Hall sensor or a Reed sensor; an acoustic or sonic sensor, in particular a microphone o an ultrasonic sensor; a thermoelectric sensor; a piezoelectric sensor; a magnetostrictive sensor; a magnetoresistive sensor; an electrochemical sensor; a resistive sensor, in particular a thermistor; a chemical sensor; an analog sensor which in particular emits analog signal; a digital sensor which in particular emits digital signal; a virtual sensor; a MEMS (Micro-Electro-Mechanical System) sensor; a touch-sensitive sensor.

The at least one sensor can be arranged on at least one of the following positions: in the inside of the medical or dental instrument part; on the outside of the medical or dental instrument part; on one or more components of the medical or dental instrument part; on a outer sleeve or gripping shell of the medical or dental instrument part; on a bearing of the medical or dental instrument part; on a printed circuit board of the medical or dental instrument part. Alternatively, the at least one sensor can be connected to and removed from the medical or dental instrument part, for example, when the at least one sensor is comprised in an element which can be coupled to the medical or dental instrument part.

The at least one sensor may be configured to sense at least one of the following parameters: temperature; speed; torque; force; vibration; pressure of a fluid, in particular a liquid or gas; humidity; distance; concentration of a substance, in particular in tissue or a body fluid; time; electrical impedance; electrical voltage; electrical amperage; density of a material; an input, gesture or indication of a user; an input, gesture or indication of a person treated with the medical or dental instrument part.

Especially preferred the at least one sensor may comprise an accelerometer or a gyroscope. The sensor signals provided by an accelerometer or a gyroscope may in particular be used by the medical or dental instrument part controller and/or by the control, regulating or supply unit to track the position of the medical or dental instrument part and/or to control the medical or dental instrument part through gesture control and/or to navigate the medical or dental instrument part.

According to an embodiment the first shared electric line connects to a first electrical contact on an end face of the coupling device of the medical or dental instrument part, the second shared electric line connects to a second electrical contact on the end face of the coupling device of the medical or dental instrument part and the third electric line connects to a third electrical contact on the end face of the coupling device of the medical or dental instrument part. The first, second and third electrical contacts can be coupled to respective contacts of the supply tube for supply of electrical power to the electromagnetic radiation emitting device and to the medical or dental instrument part controller and for transmission of the sensor signal and preferably of the identification data and/or operating data and/or care data. The first, second and third electrical contacts are arranged on a shared protrusion projecting from the end face of the coupling device. According to an embodiment a medical or dental treatment device comprises a medical or dental instrument part as described above; a shared electrical power source for supplying electrical power to the medical or dental instrument part, in particular to the electromagnetic radiation emitting device and to the medical or dental instrument part controller and to the at least one sensor if the sensor needs power to operate; and a control, regulating or supply unit for receiving the sensor signal of the at least one sensor and preferably for exchanging identification data and/or operating data and/or care data of the instrument part with the medical or dental instrument part controller. Preferably, the shared electrical power source comprises a constant voltage source.

The control, regulating or supply unit is in particular configured to at least one of: operate the instrument part on the basis of the sensor signal received from the at least one sensor; store the sensor signal received from the at least one sensor; display a value or parameter derived from the sensor signal received from the at least one sensor.

According to an embodiment a medical or dental treatment device comprises a first medical or dental instrument part comprising a first medical or dental instrument part controller operable with electrical power, an electromagnetic radiation emitting device and at least one first sensor which is configured to generate a first sensor signal; a second medical or dental instrument part which is distinct from the first medical or dental instrument part and comprises a second medical or dental instrument part controller operable with electrical power and at least one second sensor which is configured to generate a second sensor signal; and three electrical lines comprising a first shared electric line, a second shared electric line and a third electric line. The first medical or dental instrument part and the second medical or dental instrument part can be coupled to one another to connect via a shared supply tube to a shared electrical power source and to a shared control, regulating or supply unit. The first shared electric line and the second shared electric line connect to the first and second medical or dental instrument part controllers and to the electromagnetic radiation emitting device and supply electrical power from the shared electrical power source to the electromagnetic radiation emitting device for operating the electromagnetic radiation emitting device and to the first and second medical or dental instrument part controllers for operating the first and second medical or dental instrument part controllers. The third electric line of the three electric lines connects to the at least one first and second sensors so that the first and second sensor signals of the at least one first and second sensors can be transmitted over the third electric line to the shared control, regulating or supply unit.

According to this embodiment the electric power supply and the data transfer between the first medical or dental instrument part, the second medical or dental instrument part and the shared control, regulating or supply unit is achieved in an advantageous manner through the three electrical lines. The number of electrical lines between the medical or dental instrument parts and the shared control, regulating or supply unit is thus kept low which facilitates manufacture and reduces the manufacturing costs of the medical or dental treatment device.

The first medical or dental instrument part and the second medical or dental instrument part may comprise one of the following, but not the same elements: a medical or dental element that can be held in a hand, e.g., a hand grip element, a straight handpiece, an angled or bent handpiece or a contra-angled handpiece; an adapter; an attachment; a coupling element; a drive element, e.g., an air motor or an electric motor, in particular to drive a component of or a tool attachable to a medical or dental element that can be held in a hand; a supply tube, in particular a coupling portion of a supply tube which is configured to couple to a medical or dental element that can be held in a hand or to a drive element.

The first medical or dental instrument part corresponds to the embodiments of the medical or dental instrument parts described above and may comprise one or more of the elements, features or functions described in connection with these previous embodiments. In particular, the first medical or dental instrument part controller, the electromagnetic radiation emitting device and the at least one first sensor of the first medical or dental instrument part correspond to the respective embodiments of the medical or dental instrument part controller, the at least one sensor and the electromagnetic radiation emitting device described above and thus may comprise one or more of the elements, features or functions described in connection with these previous embodiments.

Correspondingly, the second medical or dental instrument part controller and the at least one second sensor of the second medical or dental instrument part correspond to the embodiments of the medical or dental instrument part controllers and the at least one sensor described above and thus may comprise one or more of the elements, features or functions described in connection with these previous embodiments.

These and other embodiments will be described below with reference to the following drawings.

DETAILED DESCRIPTION

Figures 1, 2, 3:
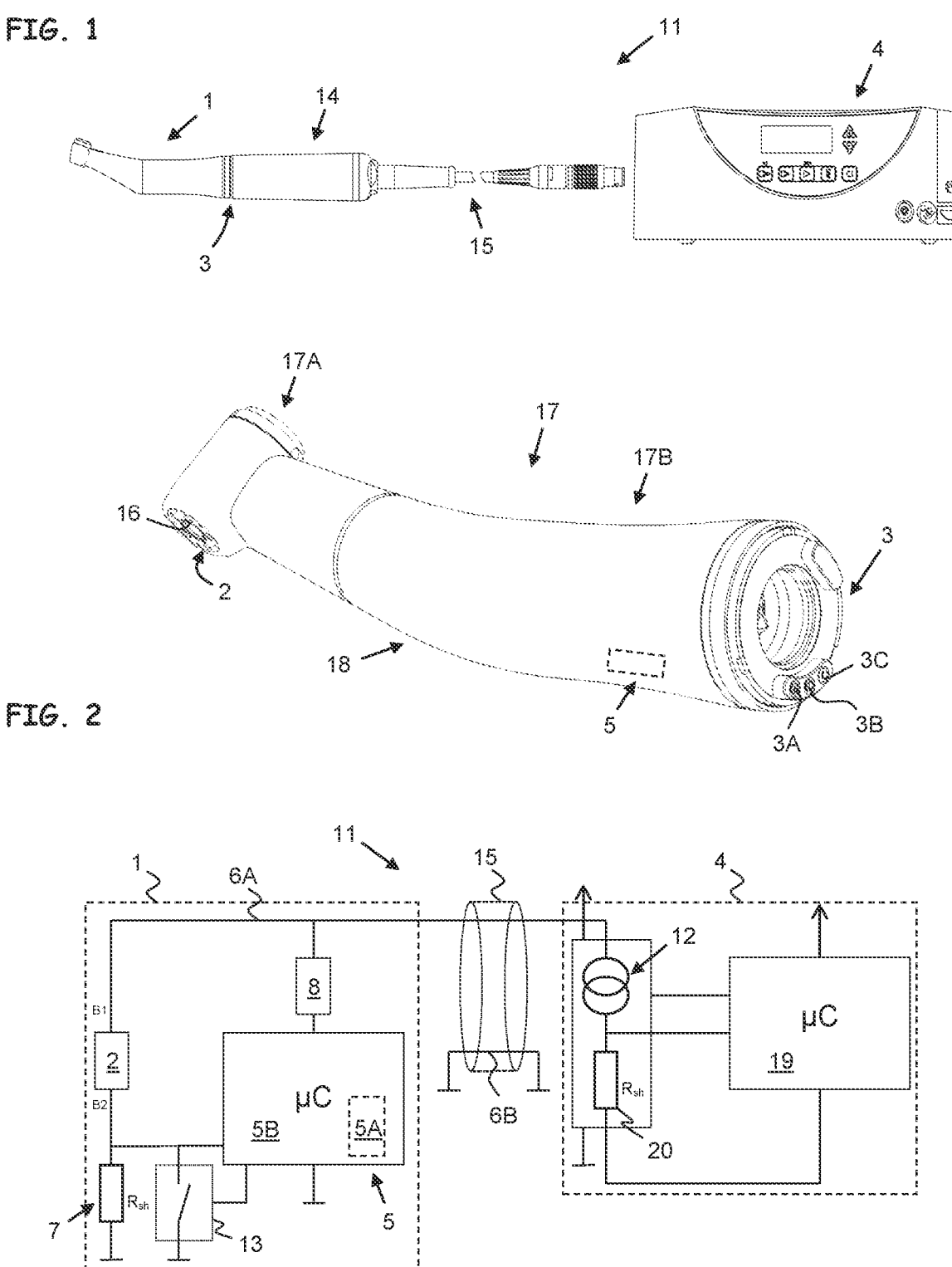
FIG. 1 shows a medical or dental treatment device comprising: a medical or dental instrument part with a lighting device, a memory device and at least one joint electrical line for supplying electrical power to the lighting device and the memory device, a drive device, a supply tube and a control, regulating or supply unit with an electrical power source for supplying electrical power to the lighting device and to the memory device.
FIG. 2 shows the medical or dental instrument part of FIG. 1.
FIG. 3 shows a schematic diagram of a first embodiment of an electrical switching circuit or current circuit having at least one joint electrical line for supplying a lighting device and a memory device.

FIG. 1 shows a medical or dental treatment device 11, comprising a medical or dental instrument part 1, a drive unit 14, a control, regulating or supply unit 4 and a supply tube 15 connecting the instrument part 1 to the control, regulating or supply unit 4. The instrument part 1 is releasably connected to the control, regulating or supply unit 4 by a coupling device 3.

The instrument part 1 shown on an enlarged scale in FIG. 2 is formed by a bent handpiece or contra-angle handpiece 17. The handpiece 17 comprises a handpiece head 17A, in which a tool holder for fastening a tool, releasably in particular, is disposed as well as a handle part 17B for holding the handpiece 17 with one hand. The coupling device 3 and/or at least a portion thereof is/are disposed on the free or proximal end of the handle part 17B.

The drive unit 14 comprises, for example, an electric motor or an air motor, designed as separate components releasable from the handpiece 17 (as shown in FIG. 1) or integrated into the handpiece 17. However, the drive unit 14 may also comprise an impeller disposed in the handpiece 17, in particular in the handpiece head 17A and driven by a propellant gas. The handpiece 17 may thus be motor operated and may have at least one driveshaft for transmitting a drive movement to the tool or may be designed to be operated by propellant gas with an impeller. In both cases the handpiece 17 comprises at least one drive element that can be set in rotation for driving a tool that is connectable to the handpiece.

The handpiece 17 additionally comprises a lighting device 2, which is preferably disposed on the handpiece head 17A or adjacent thereto. The lighting device 2 shown in FIG. 2 comprises in particular a plurality of optical semiconductor elements (LEDs) disposed in a ring around the tool receptacle opening 16 of the handpiece head 17A.

In addition, openings for dispensing a medium, for example, water and/or air, are preferably disposed around the tool receptacle opening 16, preferably in alternation with the optical semiconductor elements. The openings for dispensing a medium are connected by at least one media line in the handpiece 17 to the control, regulating or supply unit 4 for supplying at least one medium.

In addition, a memory device for storing identification data and/or operating data and/or care data of the instrument part 1 or the handpiece 17 and which can be operated with electric power is disposed in the instrument part 1 or the handpiece 17. The memory device 5 may be disposed in the handpiece head 17A or in the handle part 178 or one part of the memory device 5 may be provided in the handpiece head 17A and another in the handle part 17B. Within the handle part 17B the memory device 5 or a portion thereof is disposed, for example, on its proximal or free end, in particular in or on the coupling device 3, in a section of the handle part 178 connected directly to the handpiece head 17A or in a bend 18 of the handle part 176.

Figures 4, 5A, 5B, 5C, 6:
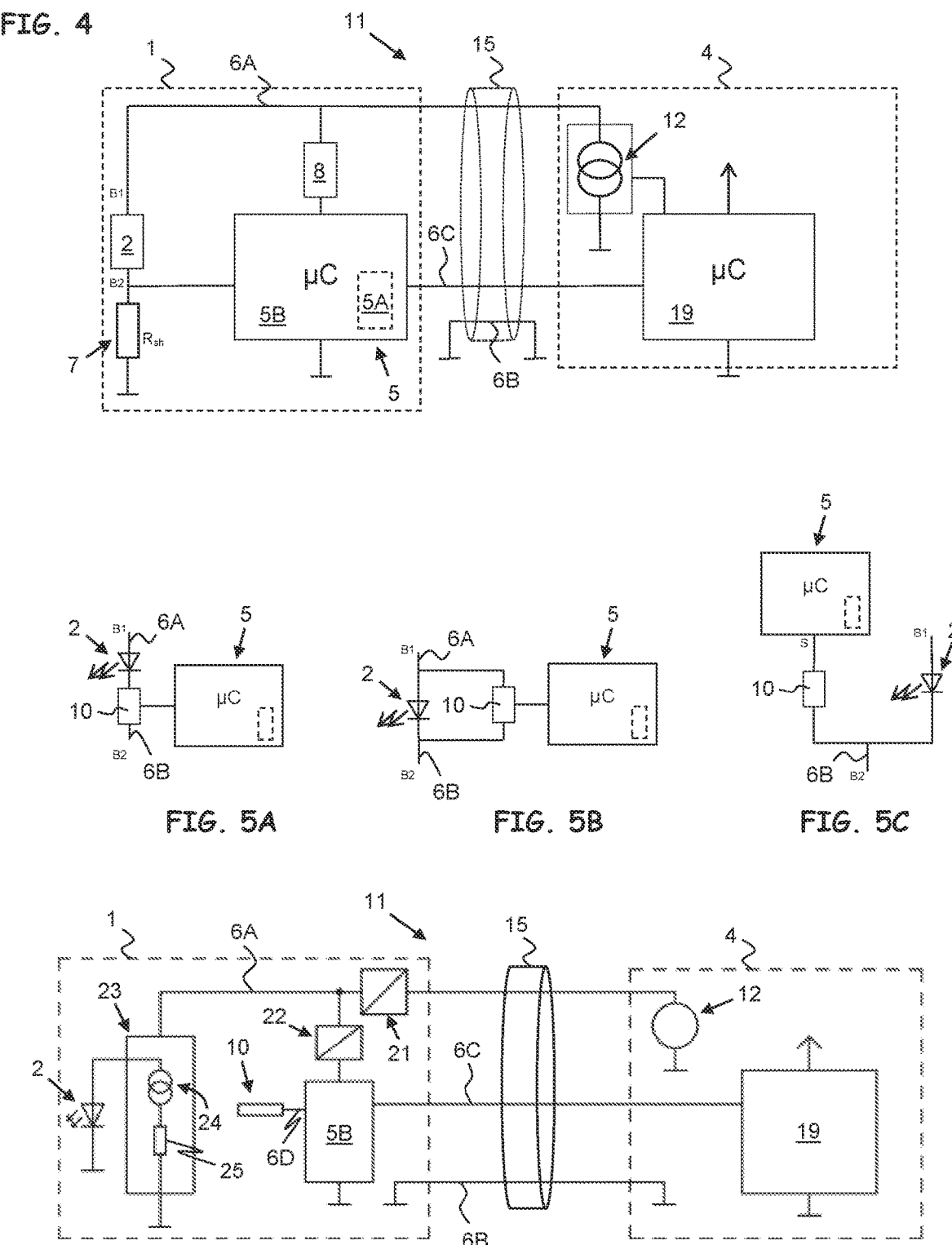
FIG. 4 shows a schematic diagram of a second embodiment of an electrical switching circuit or current circuit having at least one joint electrical line for supplying a lighting device and a memory device.
FIGS. 5A-5C show three different embodiments of a lighting device and a sensor for an electrical switching circuit or current circuit of FIG. 4 or 5.
FIG. 6 shows a schematic diagram of an embodiment of an electric circuit connecting a medical or dental instrument part with a control, regulating or supply unit, the electric circuit having two electrical lines for supplying electrical power to a radiation emitting device, a controller and optionally to a sensor of the medical or dental instrument part and another electrical line for connecting the sensor to the control, regulating or supply unit for the transmission of a sensor signal.

The memory device 5 comprises in particular a memory element 5A and a microcontroller 56, in particular for operating the memory element 5A (see FIGS. 3 and 4).

As can be seen in particular from FIGS. 3 and 4, the instrument part 1 or the handpiece 17 additionally comprises at least one (joint) electrical line 6A, 68, which is provided for supplying electrical power to the lighting device 2 provided on the handpiece 17 for operation of the lighting device 2 and for supply of electrical power to the memory device for operation of the memory device 5. The at least one (joint) electrical line 6A, 68 connects the lighting device 2 and the memory device 5 to an electrical power source 12, in particular a constant current source, which is disposed in the control, regulating or supply unit 4 and which is designed to supply electrical power to the lighting device 2 and to the memory device 5. As can also be seen from FIGS. 3 and 4, the at least one (joint) electrical line 6A, 66 extends through the supply tube 15 up to or into the control, regulating or supply unit 4.

The at least one (joint) electrical line 6A, 6B thus electrically connects the lighting device 2 and the memory device 5 to the control, regulating or supply unit 4, in particular its electrical power source 12 and microcontroller 19, thereby forming an electrical switching circuit, control circuit, regulating circuit or supply circuit. Preferably the switching circuit, control circuit, regulating circuit or supply circuit also includes at least one sensor 10, as described in detail further below.

The electrical power source 12 in the form of a constant current source supplies electrical power at a constant electrical amperage to the instrument part 1 or the handpiece 17. For the lighting device 2 comprising at least one optical semiconductor, this forms an optimal power supply. However, the memory device 5, in particular the microcontroller 5B, requires an electrical supply at a constant electrical voltage. Therefore, a device 8 for voltage processing is provided, which is assigned to the memory device 5, in particular the microcontroller 5B, and is designed to convert the electrical power at a constant electrical amperage received from the electrical power source 12 (over the electrical line 6A, 6B) into electrical power at a constant electrical voltage and to supply this converted power to the memory device 5. The device 8 for voltage processing is disposed in the instrument part 1 or the handle 17 in particular.

According to FIG. 3, two (joint) electrical lines 6A, 6B are provided for supplying electrical power to the lighting device 2 and to the memory device 5, as described above. In addition, the two electrical lines 6A, 6B are provided for transmitting identification data and/or operating data and/or care data between the memory device 5 and the control, regulating or supply unit 4 that can be connected to the instrument part 1 or handpiece 17. In other words, no more than the two (joint) electrical lines 6A, 6B are provided for supplying electrical power to the lighting device 2 and to the memory device 5 and for the data transmission. Accordingly, the control, regulating or supply unit 4 is designed for exchanging identification data and/or operating data and/or care data of the instrument part 1 with the memory device 5.

An electrical switching element 13, which is assigned to the memory device 5 is provided for transmission of identification data and/or operating data and/or care data from the memory device 5 to the control, regulating or supply unit 4, i.e., for readout of data from the memory device 5. As already described above, the switching element 13 is designed to cause or trigger changes of an electrical current parameter, in particular the electrical voltage or the electrical load, in particular by short circuiting a shunt resistor 7. The changes in the electrical current parameter (digitally) define the transmitted data. The control, regulating or supply unit 4, in particular its microcontroller 19 is/are designed to detect or equalize the changes in the electrical current parameter and, on this basis, to detect or read out the (digitally) transmitted identification data and/or operating data and/or care data.

In addition, a shunt resistor 7 is provided in the instrument part 1 or handpiece 17 which is designed to process changes in the electrical amperage for transmission of identification data and/or operating data and/or care data between the memory device 5 and the control, regulating or supply unit 4 that can be connected to the instrument part 1. As already described above, the shunt resistor 7 is provided for storing data in the memory device 5, in particular for transmitting data from the control, regulating or supply unit 4 to the memory device 5.

Another shunt resistor 20 is assigned to the control, regulating or supply unit 4, in particular to the microcontroller 19 of the control, regulating or supply unit 4.

According to FIG. 4 two (joint) electrical lines 6A, 6B are provided for supplying electrical power to the lighting device 2 and to the memory device 5, as described above. A separate line 6C or a data line is provided for transmission of identification data and/or operating data and/or care data between the memory device 5 and the control, regulating or supply unit 4 that can be connected to the instrument part 1 or handpiece 17. In other words, three lines are provided for supplying electrical power to the lighting device 2 and to the memory device 5 and for the data transmission, namely the two (joint) electrical lines 6A, 68 for supplying electrical power and the separate line 6C for transmitting the data as described above.

The separate data line 6C may be embodied as an electrical line for transmitting electrical (data) signals or as an optical line, for example, as a glass fiber for transmitting optical (data) signals. The separate line 6C extends through the instrument part 1 or the handpiece 17 and the supply tube 15 up to or into the control, regulating or supply unit 4.

Electrical contacts 3A, 38, which are connected to the at least one joint electrical line 6A, 68, are provided on the coupling device 3 of the instrument part 1 or of the handpiece 17, in particular on the end face of the coupling device 3 (see FIG. 2). These releasable electrical contacts 3A, 3B connect the lighting device 2 and the memory device 5 electrically to the control, regulating or supply unit 4, in particular to the power source 12 and microcontroller 19 thereof. If only two joint electrical lines 6A, 6B are provide for transmitting the electrical power and the data, as described above, then accordingly only these two electrical contacts 3A, 36 are provided on the coupling device 3. If at least one separate optical or electrical line 6C is provided for transmitting identification data and/or operating data and/or care data, then another optical or electrical contact 3C, which is connected to this at least one separate line 6C for the data transmission, is provided accordingly.

The at least one electrical contact or contacts are preferably releasably connected to the control, regulating or supply unit 4. The at least one electrical contact is, for example, designed as a pin-shaped electrical contact, as a spring contact, as a sliding contact or as an annular electrical contact surrounding a component of the coupling device.

Preferably at least one sensor 10 is provided in the medical or dental instrument part 1 or handpiece 17 which is designed to detect an operating state of the instrument part 1 or the handpiece 17 and to generate a sensor signal. The sensor 10 comprises, for example, a temperature sensor or a speed sensor for measuring the rotational speed of a drive element of the instrument part 1/handpiece 17. FIGS. 5A-5C show different arrangements of the sensor 10.

The at least one sensor 10 is electrically connect to the at least one electrical line 6A, 6B so that the sensor signal of the sensor 10 and/or electrical power for operating the sensor can be transmitted over the at least one electrical line 6A, 66.

The at least one sensor 10 is preferably also electrically connected to the memory device 5, in particular to the microcontroller 5B, so that a sensor signal of the sensor 10 in particular can be forwarded to the memory device 5. The memory device 5, in particular the microcontroller 5B is/are optionally designed (1) to forward the (analog) sensor signal of the sensor 10 preferably to the control, regulating or supply unit 4, in particular to its microcontroller 19, or (2) to convert the analog sensor signal into a digital signal and to send it to the control, regulating or supply unit 4, in particular to its microcontroller 19, or (3) to receive and process the (analog) sensor signal of the sensor 10 and to operate, regulate or control the instrument part 1/handpiece 17 or a component thereof, based on the sensor signal. Preferably, the sensor signal is forwarded to the control, regulating or supply unit 4 according to (1) or (2) over at least one of the lines 6A, 68 and 6C.

In the embodiment of FIG. 5A, the sensor 10, preferably a sensor for measuring the rotational speed, is disposed electrically in series with the lighting device 2. In the embodiment of FIG. 5B, the sensor 10, preferably a sensor for measuring the temperature, is disposed in parallel electrically with the lighting device 2. In both embodiments, the sensor and the lighting device 2 have a joint electrical power source 12 and they are electrically connected to the electrical lines 6A, 6B.

In the embodiment of FIG. 5C, the sensor 10, preferably a sensor for measuring the temperature, and the lighting device 2 are connected to different electrical power sources for supplying them with electrical power.

The invention is not limited to the embodiments illustrated and described here. Furthermore, all the features of all the embodiments that are described and shown here can be combined with one another.

Figure 7:
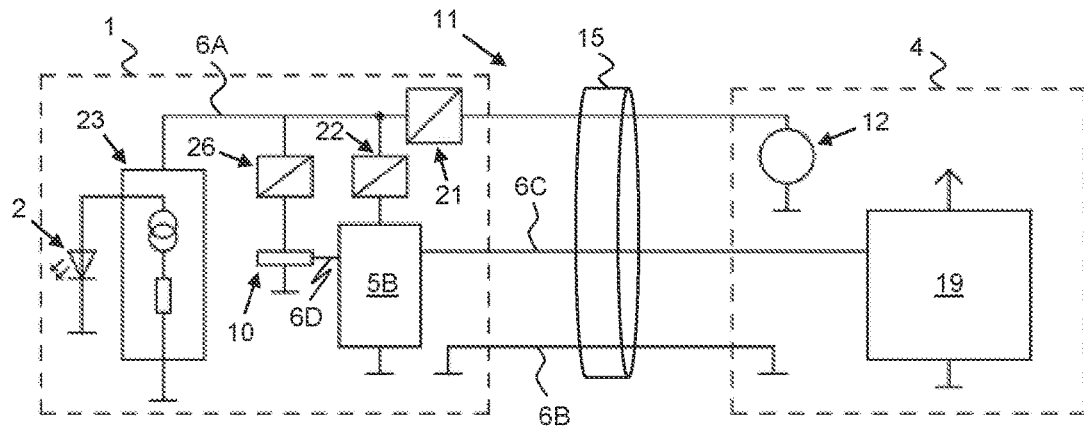
FIG. 7 shows a schematic diagram of an embodiment of an electric circuit connecting a medical or dental instrument part with a control, regulating or supply unit, the electric circuit having two electrical lines for supplying electrical power to a radiation emitting device, a controller and a sensor of the medical or dental instrument part and another electrical line for connecting the sensor to the control, regulating or supply unit for the transmission of a sensor signal.
Figure 8:
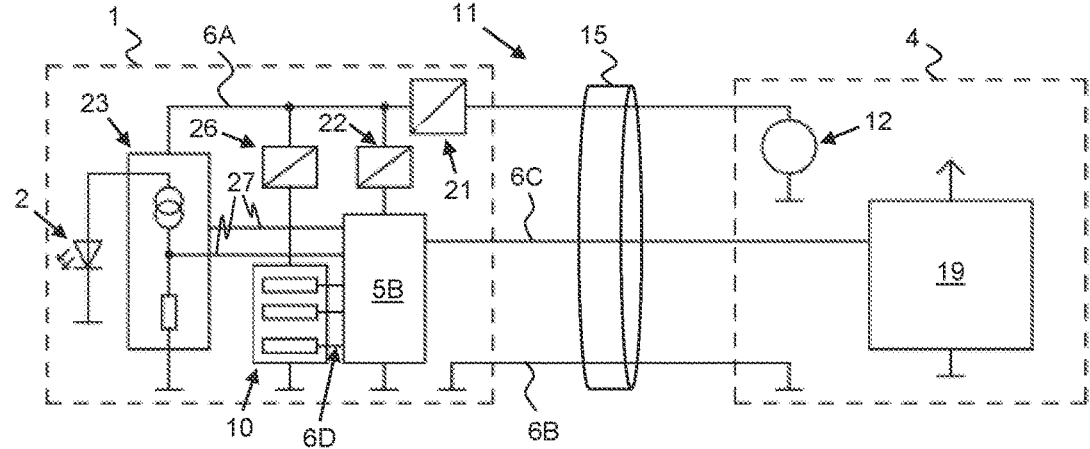
FIG. 8 shows a schematic diagram of an embodiment of an electric circuit connecting a medical or dental instrument part with a control, regulating or supply unit, the electric circuit having two electrical lines for supplying electrical power to a radiation emitting device, a controller and a plurality of sensors of the medical or dental instrument part and another electrical line for connecting the plurality of sensors to the control, regulating or supply unit for the transmission of a sensor signal.

Next, FIGS. 6-8 will be discussed, which show different embodiments of medical or dental treatment devices 11. Elements shown in FIGS. 3, 4 are also depicted in FIGS. 6-8 and have the same numerals: medical or dental instrument part 1; radiation emitting device or lighting device 2; control, regulating or supply unit 4; medical or dental instrument part controller or microcontroller 58; three electrical lines 6A, 68, 6C; shared electrical power source 12; supply tube 15 connecting the instrument part 1 to the control, regulating or supply unit 4 and holding electrical lines 6A-68, 6C; and microcontroller 19 of the control, regulating or supply unit 4. Any features, functions or properties discussed above in connection with these elements may also apply to the elements as shown in FIGS. 6-8.

Medical or dental instrument part 1 may preferably be one of a medical or dental handpiece 17, a medical or dental drive unit or electric motor 14, a medical or dental adapter, medical or dental attachment; or a medical or dental coupling device, in particular as part of a supply tube 15.

FIGS. 6-8 in addition show at least one sensor 10 which is configured to generate a sensor signal. The at least one sensor 10 is arranged in or on the medical or dental instrument part 1. Alternatively, the at least one sensor 10 can be connected to and removed from the medical or dental instrument part 1, for example, when the at least one sensor 10 is comprised in an element which can be coupled to the medical or dental instrument part 1. The at least one sensor 10 may comprise any sensor described above.

The three electrical lines 6A, 6B, 6C shown in FIGS. 6-8 comprise a first shared electric line 6A and a second shared electric line 6B which connect to the medical or dental instrument part controller 5B and to the electromagnetic radiation emitting device 2 and are configured to supply electrical power from the shared electrical power source 12 to the electromagnetic radiation emitting device 2 for operating the electromagnetic radiation emitting device 2 and to the medical or dental instrument part controller 5B for operating the medical or dental instrument part controller 5B, If the at least one sensor 10 needs power supply for operation it is also supplied by the electrical power source 12 with electric power via shared electrical lines 6A, 6B. In addition, one of electrical lines 6A, 6B, according to FIGS. 6-8 electrical line 6B, serves as ground line.

The third electric line 6C of the three electric lines connects the medical or dental instrument part controller 5B to the control, regulating or supply unit 4, in particular to microcontroller 19. The medical or dental instrument part controller 5B may comprise a memory element 5A (see FIGS. 3, 4) which is configured to store at least one of identification data, operating data or care data of the medical or dental instrument part land/or of another instrument part which is or can be coupled to medical or dental instrument part 1. Third electric line 6C is configured for data transfer, in particular of said identification data, operating data or care data, between the medical or dental instrument part controller 5B and the control, regulating or supply unit 4, in particular microcontroller 19.

Third electric line 6C also connects the at least one sensor 10 to the control, regulating or supply unit 4, in particular to microcontroller 19, so that a sensor signal of the at least one sensor 10 or data based on a sensor signal can be transmitted over the third electric line 6C to the control, regulating or supply unit 4. As can be seen in FIGS. 6-8, the sensor signal is transmitted from the at least one sensor 10 via a data or signal line 6D to the medical or dental instrument part controller 5B from where it is transmitted to the control, regulating or supply unit 4. As described above instrument part controller 5B may either be configured to only transmit the sensor signal or store and/or process the sensor signal before transmitting it to the control, regulating or supply unit 4.

The electrical lines 6A, 6B, 6C, preferably also line 6D and/or additional electrical lines, may be part of a bus system, in particular of a CAN, Flex Ray, Lin, SPI or I²C bus system, of medical or dental treatment devices 11.

The shared electrical power source 12 is arranged in the control, regulating or supply unit 4 and/or forms part of the control, regulating or supply unit 4. Preferably the shared electrical power source 12 comprises or is formed by a constant voltage source. Accordingly, the electrical power source 12 supplies electric power having a constant voltage or direct current to the medical or dental instrument part 1, in particular to the electromagnetic radiation emitting device 2 and to the medical or dental instrument part controller 5B and optionally to the at least one sensor 10.

FIGS. 6-8 also show a first device for processing electrical power 21. First device for processing electrical power 21 may comprise an electrical power converter. Depending on the electrical power supplied by the electrical power source 12 the electrical power converter may comprise a DC/DC converter or an AC/DC converter or an electronic circuit for converting electrical power.

The first device for processing electrical power 21 is preferably arranged such in the medical or dental instrument part 1 that it processes electrical power supplied by the electrical power source 12 for a plurality of or all elements of the medical or dental instrument part 1 which are supplied with electric power. Accordingly, in the FIGS. 6-8 the first device for processing electrical power 21 processes the electrical power at least for the medical or dental instrument part controller 5B and the electromagnetic radiation emitting device 2 and optionally for the at least one sensor 10 if it needs power supply for operation.

Preferably the electrical power source 12 supplies electric power having a constant voltage or direct current to the device for processing electrical power 21 which comprises a DC/DC converter. The DC/DC converter is configured to convert the voltage level of the electrical power of electrical power source 12 to a different voltage level. The device for processing electrical power 21 may alternatively or in addition comprise a filter to compensate for transmission interference of the electrical power supplied by the shared electrical power source 12 via the first and second shared electric lines 6A, 6B. Electrical power having this different voltage level and/or being filtered is then supplied to a plurality of or all elements of the medical or dental instrument part 1 which are supplied with electric power.

FIGS. 6-8 in addition show a second device for processing electrical power 22 which is assigned to medical or dental instrument part controller 5B only and/or is configured to process electrical power which is supplied to medical or dental instrument part controller 5B only. Second device for processing electrical power 22 may comprise an electrical power converter. Depending on the electrical power supplied to medical or dental instrument part controller 5B the electrical power converter may comprise a DC/DC converter or an AC/DC converter or an electronic circuit for converting electrical power.

Preferably electric power supplied to medical or dental instrument part controller 5B, in particular provided by the first device for processing electrical power 21, is direct current. Accordingly, second device for processing electrical power 22 comprises or is a DC/DC converter which is configured to convert the voltage level of the supplied electrical power to a different voltage level which matches the voltage level required by the medical or dental instrument part controller 5B. Electrical power having this different voltage level is then supplied to medical or dental instrument part controller 5B.

Radiation emitting device 2 preferably comprises at least one optical semiconductor element or light emitting diode (LED). LEDs need electrical power supply at a constant electrical amperage to operate optimally. Thus, medical or dental instrument parts 1 of FIGS. 6-8 comprise a constant current source 23 which is configured to supply electrical power at a constant electrical amperage to radiation emitting device 2. Constant current source 23 is assigned to radiation emitting device 2 only and/or supplies electrical power to radiation emitting device 2 only.

Preferably electric power provided for radiation emitting device 2, in particular supplied from the first device for processing electrical power 21, is direct current. Constant current source 23 may also be configured to adapt the level of amperage required by the radiation emitting device 2. Preferably, constant current source 23 comprises or is formed by electronics or an integrated circuit 24 which is/are configured to convert and/or match the amperage for the radiation emitting device 2 (see FIG. 6).

Constant current source 23 in addition may comprise a shunt resistor 25 (see FIG. 6). Shunt resistor 25 is preferably configured to monitor the current for radiation emitting device 2, in particular for the at least one optical semiconductor element. In particular shunt resistor prevents radiation emitting device 2 from being supplied with an electrical amperage that is too high.

Now, reference is made to the embodiment of FIG. 6: the medical or dental treatment device 11 of FIG. 6 has a single sensor 10 which connects via data or signal lines 6D to medical or dental instrument part controller 56. The sensor signals of single sensor 10 are transmitted via medical or dental instrument part controller 56 and line 6C to the control, regulating or supply unit 4, in particular microcontroller 19. The sensor signals of single sensor may be stored or processed by medical or dental instrument part controller 5B as described above. Medical or dental instrument part controller 5B may supply sensor 10 with electric power as described above, preferably via lines 6D which thus are formed as shared lines and/or are configured to transmit sensor signals and electric power.

Constant current source 23 supplies electrical power at a constant electrical amperage to radiation emitting device 2.

With reference to FIG. 7 supply of electrical power for sensor 10 here is accomplished directly, i.e. not via medical or dental instrument part controller 5B as in FIG. 6. A device for processing electrical power 26 supplied from shared electrical power source 12 via shared electrical lines 6A, 6B is assigned to sensor 10 to supply sensor 10 with the electric power that it requires. For example, the device for processing the electrical power 26 comprises a DC/DC converter.

Accordingly, line 6D serves as signal or data line only to transmit the sensor signals of sensor 10 to medical or dental instrument part controller 5B. The sensor signals of sensor 10 are transmitted via medical or dental instrument part controller 5B and line 6C to the control, regulating or supply unit 4, in particular microcontroller 19. The sensor signals of sensor 10 may be stored or processed by medical or dental instrument part controller 53 as described above.

Medical or dental treatment device 11 of FIG. 8 comprises a plurality of sensors 10. Sensors 10 may be sensors of the same type and/or sensors which measure the same property. Alternatively, at least one sensor of the plurality of sensors 10 may be a sensor of a different type and/or a sensor which measures a different property. Preferably each sensor of the plurality of sensors 10 is of a different type and/or measures a different property.

At least one sensor of the plurality of sensors 10 is supplied directly with electrical power, i.e. not via medical or dental instrument part controller 5B as in FIG. 6. A device for processing electrical power 26 supplied from shared electrical power source 12 via shared electrical lines 6A, 6B is assigned to said at least one sensor 10 to supply said sensor 10 with the electric power that it requires. For example, the device for processing the electrical power 26 comprises a DC/DC converter. Preferably more or all sensors of the plurality of sensors 10 are supplied directly with electrical power.

Alternatively, at least one sensor of the plurality of sensors 10 is supplied with electrical power via medical or dental instrument part controller 5B and line 6D as described with reference to FIG. 6.

Line 6D serves as signal or data line to transmit the sensor signals of at least one sensor or of more or all sensors of the plurality of sensors 10 to medical or dental instrument part controller 5B. The sensor signals are transmitted via medical or dental instrument part controller 5B and line 6C to the control, regulating or supply unit 4, in particular microcontroller 19. The sensor signals may be stored or processed by medical or dental instrument part controller 5B as described above.

To control the electromagnetic radiation emission of the electromagnetic radiation emitting device 2, for example the wavelength or intensity, the medical or dental instrument part controller 5B is connected to the electrical constant current source 23 which is assigned to the electromagnetic radiation emitting device 2 through electric control lines 27. The medical or dental instrument part controller 5B is configured to communicate control signals via control lines 27 to the electrical constant current source 23 to control the emission of electromagnetic radiation by the electromagnetic radiation emitting device 2. The electrical constant current source 23 of electromagnetic radiation emitting device 2 is configured to receive the control signals and to operate the electromagnetic radiation emitting device 2 according to the received control signals.

The electromagnetic radiation emitting device 2 may comprise a plurality of radiation emitting sources, e.g., LEDs, wherein the medical or dental instrument part controller 5B can be configured to control at least one radiation emitting source of the plurality of radiation emitting sources. The plurality of radiation emitting sources may preferably comprise first and second radiation emitting sources emitting first and second, different wavelengths, in particular wavelengths for diagnosis, e.g., for detecting dental caries, concrement or plaque, and wavelength for enhancing visibility for a user, wherein the medical or dental instrument part controller 5B is configured to alternatingly activate the emission of electromagnetic radiation of the first or second radiation emitting sources.

Although not shown, the control of the electromagnetic radiation emission of the electromagnetic radiation emitting device 2 by the medical or dental instrument part controller 5B through electric control lines 27 may also be implemented in the medical or dental treatment devices 11 of FIGS. 6 and 7.

Figure 9:
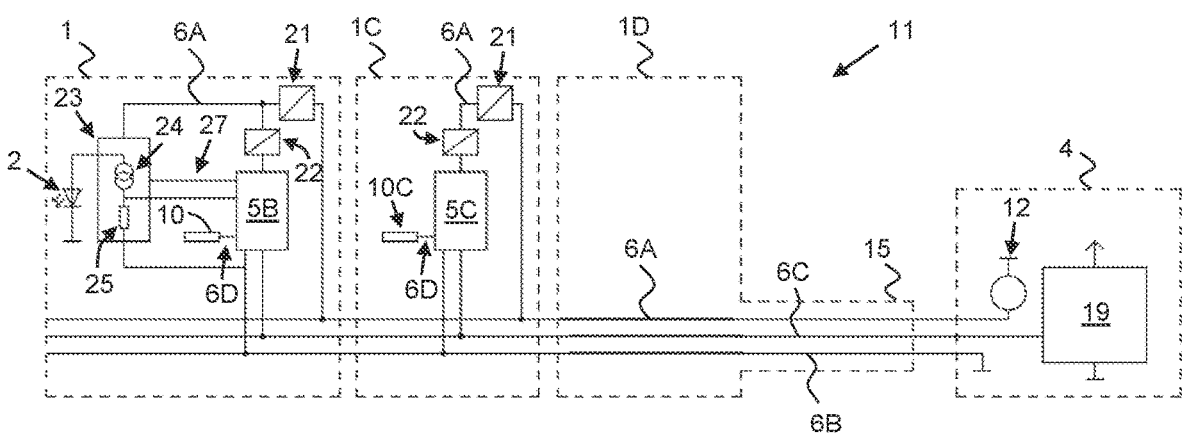
FIG. 9 shows a schematic diagram of an embodiment of an electric circuit connecting a medical or dental treatment device with a control, regulating or supply unit, the electric circuit having two electrical lines for supplying electrical power to a radiation emitting device, a plurality of controllers and a plurality of sensors of the medical or dental treatment device and another electrical line for connecting the plurality of sensors to the control, regulating or supply unit for the transmission of a sensor signal.
Figure 10:
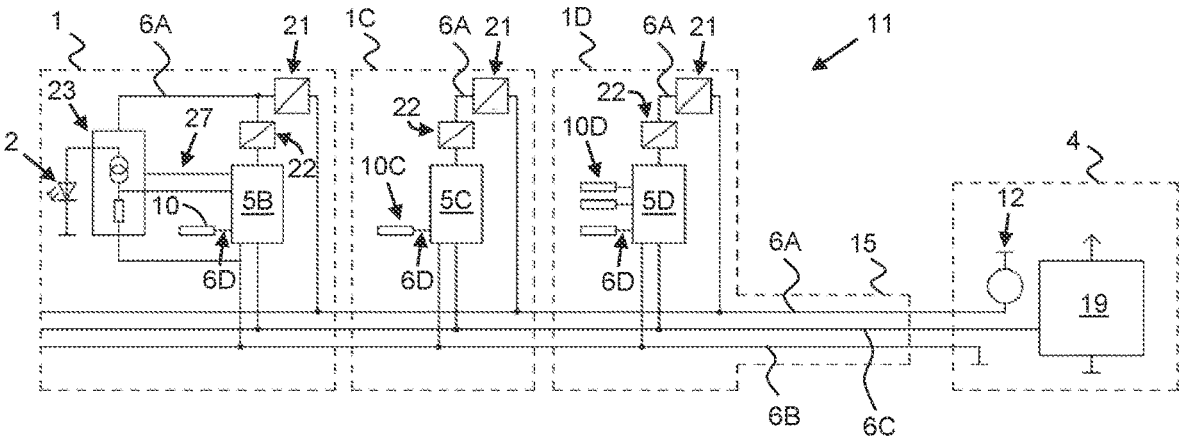
FIG. 10 shows a schematic diagram of another embodiment of an electric circuit connecting a medical or dental treatment device with a control, regulating or supply unit, the electric circuit having two electrical lines for supplying electrical power to a radiation emitting device, a plurality of controllers and a plurality of sensors of the medical or dental treatment device and another electrical line for connecting the plurality of sensors to the control, regulating or supply unit for the transmission of a sensor signal.
Figure 11:
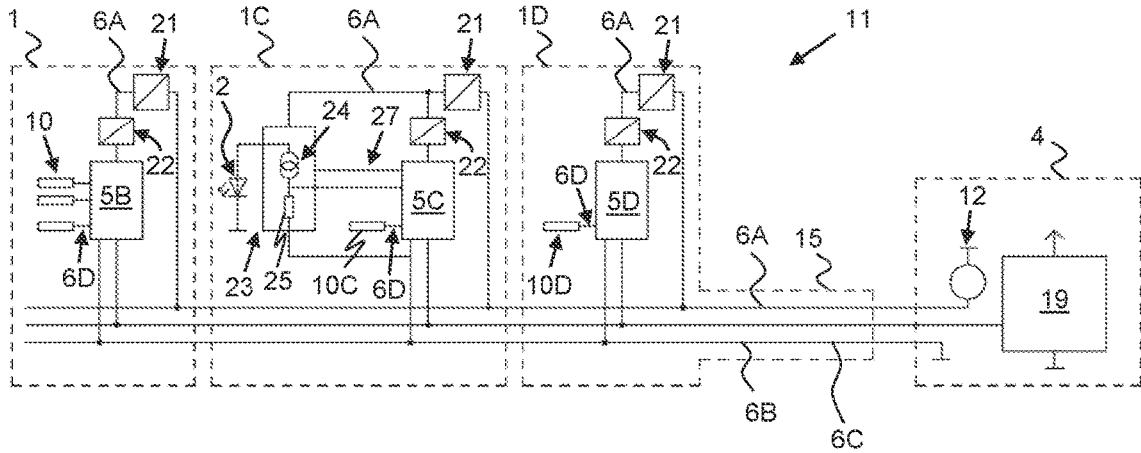
FIG. 11 shows a schematic diagram of another embodiment of an electric circuit connecting a medical or dental treatment device with a control, regulating or supply unit, the electric circuit having two electrical lines for supplying electrical power to a radiation emitting device, a plurality of controllers and a plurality of sensors of the medical or dental treatment device and another electrical line for connecting the plurality of sensors to the control, regulating or supply unit for the transmission of a sensor signal.

Reference is now made to FIGS. 9-11. These figures show embodiments of medical or dental treatment devices 11 having a plurality of medical or dental instrument parts 1, 1C, 1D. Medical or dental treatment device 11 may comprise a different number of medical or dental instrument parts 1, 1C, 1D, for example of two, three, four, five or more. These medical or dental instrument parts 1, 1C, 1D are or can be coupled, preferably releasably coupled, to form a medical or dental treatment device 11. A physical view of an embodiment of such a medical or dental treatment devices 11 is shown in FIG. 1.

Elements shown in FIGS. 3, 4 and 6-8 are also depicted in FIGS. 9-11 and have the same numerals. Any features, functions or properties discussed above in connection with these elements may also apply to the elements as shown in FIGS. 9-11.

The medical or dental instrument parts 1, 1C, 1D, in particular when coupled together, connect via supply hose 15 to (shared) control, regulating or supply unit 4 in order to transmit or exchange at least one of electrical power, mechanical power, a fluid, a medium, a substance, signals or data. Lines and/or tubes for the transmission, in particular electrical lines 6A, 6B, 6C, thus reach from the control, regulating or supply unit 4 through supply hose 15 to at least one of the medical or dental instrument parts 1, 1C, 1D. The lines may comprise optical or electrical lines.

Alternatively, lines and/or tubes for the transmission, in particular electrical lines 6A, 6B, 6C, reach from control, regulating or supply unit 4 through supply hose 15 to a plurality or all of the medical or dental instrument parts 1, 1C, 1D.

Electrical lines 6A, 6B, 6C preferably form part of a bus system, in particular a CAN, Flex Ray, Lin, SPI or I²C bus system, wherein a plurality of components of the medical or dental instrument parts 1, 1C, 1D which are configured to receive electrical power and/or to communicate with one another and/or with (shared) control, regulating or supply unit 4 connect and communicate and/or are energized through electrical lines 6A, 6B, 6C. The plurality of components of the medical or dental instrument parts 1, 1C, 1D may comprise for example one or more electromagnetic radiation emitting devices 2, one or more medical or dental instrument part controllers 5B, one or more memory elements 5A, one or more sensors 10. The components of this plurality of components may either be arranged in a single medical or dental instrument part 1, 1C, 1D or in a plurality of medical or dental instrument parts 1, 1C, 1D which are or can be coupled to form medical or dental treatment devices 11.

According to an especially preferred embodiment medical or dental instrument part 1 may comprise a medical or dental handpiece 17, in particular as described above, medical or dental instrument part 1C may comprise a medical or dental drive unit or electric motor 14, in particular as described above, and medical or dental instrument part 10 may comprise a medical or dental coupling device. Medical or dental coupling device 1D may either be formed in one piece with supply tube 15 or may be a separate part which couples releasably to supply tube 15.

It is however expressly pointed out that at least one of the medical or dental instrument parts 1, 1C, 10 may comprise a different function and/or at least one different component. Medical or dental treatment device 11 may for example comprise a medical or dental instrument part 1 having an electromagnetic radiation emitting device 2 and an optical sensor 10, in particular a camera, and a medical or dental instrument part 1C or 1D having at least one additional sensor 10.

Medical or dental instrument part 1 of FIG. 9 and medical or dental instrument part 1 of FIG. 10 comprise components which have been described above or correspond to components which have been described above: radiation emitting device or lighting device 2; medical or dental instrument part controller or microcontroller 56; electrical lines 6A, 66, 6C; sensor 10; first device for processing electrical power 21; second device for processing electrical power 22; electrical constant current source 23 of electromagnetic radiation emitting device 2 with electronics 24 and shunt resistor 25; electric control lines 27. Sensor 10 connects via line 6D to medical or dental instrument part controller or microcontroller 5B, wherein line 6D may be configured to either transmit sensor signals only or in addition transmit electrical power to the sensor 10, depending on the type of sensor.

Medical or dental instrument part 1C of FIG. 9 and medical or dental instrument part 1C of FIG. 10 comprise components which have been described above or correspond to components which have been described above: medical or dental instrument part controller or microcontroller 5C; electrical lines 6A, 6B, 6C; sensor 10C; at least one device for processing electrical power 21, 22. Sensor 10C connects via line 60 to medical or dental instrument part controller or microcontroller 5C, wherein line 6D may be configured to either transmit sensor signals only or in addition transmit electrical power to the sensor 10, depending on the type of sensor.

Medical or dental instrument part 1D of FIG. 9 comprises a coupling device, preferably formed in one piece with supply hose 15. According to this embodiment medical or dental instrument part 1D only comprises electrical lines 6A, 6B, 6C.

Medical or dental instrument part 1D of FIG. 10 comprises a coupling device which may either be formed in one piece with supply hose 15 or may constitute a separate device which is releasable from supply tube 15. Medical or dental instrument part 1D of FIG. 10 comprises components which have been described above or correspond to components which have been described above: medical or dental instrument part controller or microcontroller 5D; electrical lines 6A, 6B, 6C; a plurality of sensors 10D; at least one device for processing electrical power 21, 22. Sensors 10D connect via lines 6D to medical or dental instrument part controller or microcontroller 5D, wherein each respective line 6D may be configured to either transmit sensor signals only or in addition transmit electrical power to one of the sensors of the plurality of sensors 10, depending on the type of sensor.

Medical or dental instrument part 1 of FIG. 11 comprises components which have been described above or correspond to components which have been described above: medical or dental instrument part controller or microcontroller 5B; electrical lines 6A, 6B, 6C; a plurality of sensors 10; at least one device for processing electrical power 21, 22. Sensors 10D connect via lines 6D to medical or dental instrument part controller or microcontroller 5D, wherein each respective line 6D may be configured to either transmit sensor signals only or in addition transmit electrical power to one of the sensors of the plurality of sensors 10, depending on the type of sensor.

Medical or dental instrument part 1C of FIG. 11 comprises components which have been described above or correspond to components which have been described above: radiation emitting device or lighting device 2; medical or dental instrument part controller or microcontroller 5C; electrical lines 6A, 6B, 6C; sensor 10; first device for processing electrical power 21; second device for processing electrical power 22; electrical constant current source 23 of electromagnetic radiation emitting device 2 with electronics 24 and shunt resistor 25; electric control lines 27. Sensor 10 connects via line 6D to medical or dental instrument part controller or microcontroller 5C, wherein line 6D may be configured to either transmit sensor signals only or in addition transmit electrical power to the sensor 10, depending on the type of sensor.

Medical or dental instrument part 1D of FIG. 11 comprises components which have been described above or correspond to components which have been described above: medical or dental instrument part controller or microcontroller 5D; electrical lines 6A, 6B, 6C; sensor 10D; at least one device for processing electrical power 21, 22. Sensor 10D connects via line 6D to medical or dental instrument part controller or microcontroller 5D, wherein line 6D may be configured to either transmit sensor signals only or in addition transmit electrical power to the sensor 10, depending on the type of sensor.

Medical or dental instrument part 1 and/or 1C of FIG. 11 may comprise an optical radiation or light guide to convey electromagnetic radiation emitted by electromagnetic radiation emitting device 2 through medical or dental instrument part 1 and/or 1C. Thus, the electromagnetic radiation may be radiated from instrument part 1.

In FIGS. 9-11 a device for processing electrical power 21 is provided in each medical or dental instrument part 1, 1C and 1D. Alternatively, it is also possible to provide only one such device 21 per medical or dental treatment device 11, which processes electrical power received from power source 12 and provides the processed electrical power via electrical lines 6A, 6B to all components which are supplied with electrical power of medical or dental treatment device 11, in particular to components 2, 5B, 5C, 5D and 10. Such a single device 21 is preferably arranged close to supply tube 15, in particular in medical or dental instrument part 1D. Such a single device 21 comprises for example an AC/DC converter, rectifier, a DC/AC converter, inverter, electronics or an integrated circuit which process the electrical power accordingly.

Electrical lines 6A, 6B, 6C of FIGS. 9-11 extend from (shared) control, regulating or supply unit 4 through supply tube 15 and each of medical or dental instrument parts 1, 1C, 1D. Components 2; 5B; 10; 21; 22; 23; 5C; 10C; 5D, 10D connect to electrical lines 6A, 6B, 6C, preferably via electrical branch lines, and receive electrical power and/or communicate through electrical lines 6A, 6B, 6C.

Communication via electrical lines 6A, 6B, 6C may comprise at least one of: transmission of signals of sensors 10, 10C, 10D to control, regulating or supply unit 4; transmission of signals from control, regulating or supply unit 4 to at least one of sensors 10, 10C, 10D, in particular if at least one of sensors 10, 10C, 100 comprises a digital sensor; transmission of identification data and/or operating and/or care data from at least one of medical or dental instrument part controller 5B, 5C, 5D or memory element 5A to control, regulating or supply unit 4; transmission of data from control, regulating or supply unit 4 to at least one of medical or dental instrument part controllers 5B, 5C, 5D or memory element 5A; transmission of signals or data between at least two dental instrument part controllers 5B, 5C, 5D; transmission of signals or data between at least two sensors 10, 10C, 10D, in particular if one of the sensors 10, 10C, 100 comprises a virtual sensor.

To accomplish electrical power transfer and communication as described above electrical lines 6A, 6B, 6C, sensors 10, 10C, 100, medical or dental instrument part controllers 5B, 5C, 5D, memory element 5A and control, regulating or supply unit 4, in particular microcontroller 19, form a bus system, in particular a bus system as described above.

In view of the many possible embodiments to which the disclosed principles may be applied, it should be recognized that the illustrated embodiments are only preferred examples and should not be taken as limiting the scope of protection. Rather, the scope of protection is defined by the following claims. We therefore claim all that comes within the scope and spirit of these claims.

What is claimed is:

1. A medical or dental treatment device, comprising:
a first medical or dental instrument part comprising a first medical or dental instrument part controller operable with electrical power,
a second medical or dental instrument part which is distinct from the first medical or dental instrument part and comprises a second medical or dental instrument part controller operable with electrical power,
at least one sensor which is arranged in one of the first or second medical or dental instrument part and is configured to generate a sensor signal,
two shared electrical lines comprising a first shared electric line and a second shared electric line, wherein
the first medical or dental instrument part and the second medical or dental instrument part can be coupled to one another to connect via a shared supply tube to a shared electrical power source and to a shared control, regulating or supply unit, wherein the first shared electric line and the second shared electric line connect to the first and second medical or dental instrument part controllers and supply electrical power from the shared electrical power source to the first and second medical or dental instrument part controllers for operating the first and second medical or dental instrument part controllers, and wherein
at least one of the first shared electric line or the second shared electric line connects to the at least one sensor to transmit the sensor signal of the at least one sensor over the first or second shared electric line to the shared control, regulating or supply unit.

2. The medical or dental treatment device according to claim 1, wherein the at least one sensor connects to the first or second medical or dental instrument part controller so that the sensor signal of the at least one sensor can be transmitted via the first or second medical or dental instrument part controller and at least one of the first or second shared electric line to the shared control, regulating or supply unit.

3. The medical or dental treatment device according to claim 2, wherein the first or second medical or dental instrument part controller is configured to process and/or store the sensor signal of the at least one sensor.

4. The medical or dental treatment device according to claim 2, wherein the first or second medical or dental instrument part controller operates or regulates or controls at least one component of the medical or dental treatment device based on the sensor signal.

5. The medical or dental treatment device according to claim 1, wherein the first medical or dental instrument part controller comprises a first memory element for storing identification data and/or operating and/or care data of the first medical or dental instrument part, wherein the first memory element connects to at least one of the first or second shared electric lines so that the identification data and/or operating and/or care data of the first medical or dental instrument part can be transmitted over at least one of the first or second shared electric line between the shared control, regulating or supply unit and the first memory element.

6. The medical or dental treatment device according to claim 1, wherein the second medical or dental instrument part controller comprises a second memory element for storing identification data and/or operating and/or care data of the second medical or dental instrument part, wherein the second memory element connects to at least one of the first or second shared electric lines so that the identification data and/or operating and/or care data of the second medical or dental instrument part can be transmitted over at least one of the first or second shared electric line between the shared control, regulating or supply unit and the second memory element.

7. The medical or dental treatment device according to claim 1, comprising a device for processing electrical power which is configured to process the electrical power supplied by the shared electrical power source via the first and second shared electric lines to the medical or dental treatment device.

8. The medical or dental treatment device according to claim 1, wherein the first and second shared electric lines connect the at least one sensor to the shared electrical power source to supply electrical power to the at least one sensor.

9. The medical or dental treatment device according to claim 1, wherein the first or second medical or dental instrument part controller is configured to supply electrical power to the at least one sensor.

10. The medical or dental treatment device according to claim 1, wherein the at least one sensor comprises at least one of: a mechanical sensor; a capacitive sensor; an inductive sensor; an optical or optoelectronic sensor; a magnetic sensor; an acoustic or sonic sensor; a thermoelectric sensor; a piezoelectric sensor; a magnetostrictive sensor; a magnetoresistive sensor; an electrochemical sensor; a resistive sensor; a chemical sensor; or a touch-sensitive sensor.

11. The medical or dental treatment device according to claim 1, wherein the at least one sensor comprises at least one of: an analog sensor; a digital sensor; or a virtual sensor.

12. The medical or dental treatment device according to claim 1, wherein the at least one sensor comprises an accelerometer or a gyroscope.

13. The medical or dental treatment device according to claim 1, wherein the at least one sensor comprises a temperature sensor for measuring a temperature of at least one component of the medical or dental treatment device or of at least one component attached to the medical or dental treatment device or of a workpiece worked by the medical or dental treatment device.

14. The medical or dental treatment device according to claim 1, wherein the at least one sensor comprises a speed sensor for measuring a rotational speed of at least one component of the medical or dental treatment device or of at least one component attached to the medical or dental treatment device.

15. The medical or dental treatment device according to claim 1, wherein the first shared electric line connects to a first electrical contact on an end face of the first medical or dental instrument part and the second shared electric line connects to a second electrical contact on the end face of the first medical or dental instrument part, wherein the first and second electrical contacts can be coupled to respective contacts of the second medical or dental instrument part or of the shared supply tube for supply of electrical power to the first medical or dental instrument part controller, wherein the first and second electrical contacts are arranged on a shared protrusion projecting from the end face of the first medical or dental instrument part.

16. The medical or dental treatment device according to claim 1, further comprising the shared electrical power source having a constant voltage source.

17. The medical or dental treatment device according to claim 1, further comprising a control, regulating or supply unit which is configured to operate the first or second medical or dental instrument part on the basis of the sensor signal received from the at least one sensor.

18. The medical or dental treatment device according to claim 1, wherein the at least one sensor is a first sensor arranged in one of the first or second medical or dental instrument part and configured to generate a first sensor signal, wherein the medical or dental treatment device comprises a second sensor arranged in the other of the first or second medical or dental instrument part and configured to generate a second sensor signal, and wherein at least one of the first or second shared electric line connects to the second sensor to transmit the second sensor signal of the second sensor over the first or second shared electric line to the shared control, regulating or supply unit.

19. The medical or dental treatment device according to claim 1, wherein the first medical or dental instrument part is a medical or dental handpiece and the second medical or dental instrument part is a motor to drive a tool holder of the medical or dental handpiece.

20. The medical or dental treatment device according to claim 19, wherein the at least one sensor is arranged in the medical or dental handpiece and comprises an accelerometer or a gyroscope.

\* \* \* \* \*